US00PP09307P

United States Patent [19]

Hanes

[11] Patent Number: Plant 9,307

[45] Date of Patent: Sep. 26, 1995

[54] GERANIUM NAMED 'AMERICANA DARK RED'

[75] Inventor: Mitchell E. Hanes, Morgan Hill, Calif.

[73] Assignee: Goldsmith Seeds, Inc., Gilroy, Calif.

[21] Appl. No.: 364,876

[22] Filed: Dec. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Henderson & Sturm

[57] ABSTRACT

A new geranium cultivar particularly distinguished by green foliage with faint zonation, dark red color, and semi-double flowers on large umbels, fast rooting and vigorous growth.

1 Drawing Sheet

BACKGROUND OF THE NEW PLANT

The present invention comprises a new and distinct cultivar of geranium, botanically known as *Pelargonium hortorum* Bailey, and hereinafter referred to by the cultivar named Americana Dark Red. The new cultivar is propagated from a seedling resulting from the cross of a seed parent 3459-3, a dark red, single flower, breeding line and a second breeding line that was used as the pollen parent known as 3126-3. This parent has a dark red, semi-double flower form.

Americana Dark Red is a product of a planned breeding program intended to create new geranium cultivars with dark red colored flowers, semi-double flower form, green foliage, vigorous growth and superior cutting productivity.

The new cultivar was created in 1992 in Gilroy, Calif. and has been repeatedly asexually reproduced by cuttings in Gilroy, Calif. and Guatemala over a two year period. It has also been trailed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
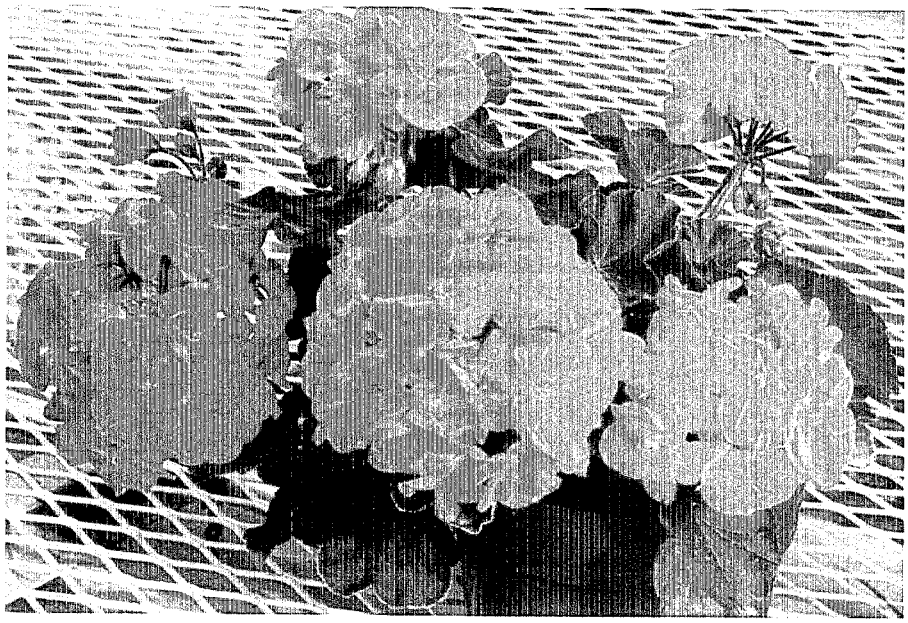
FIG. 1 shows overall plant habit.
Figure 2:
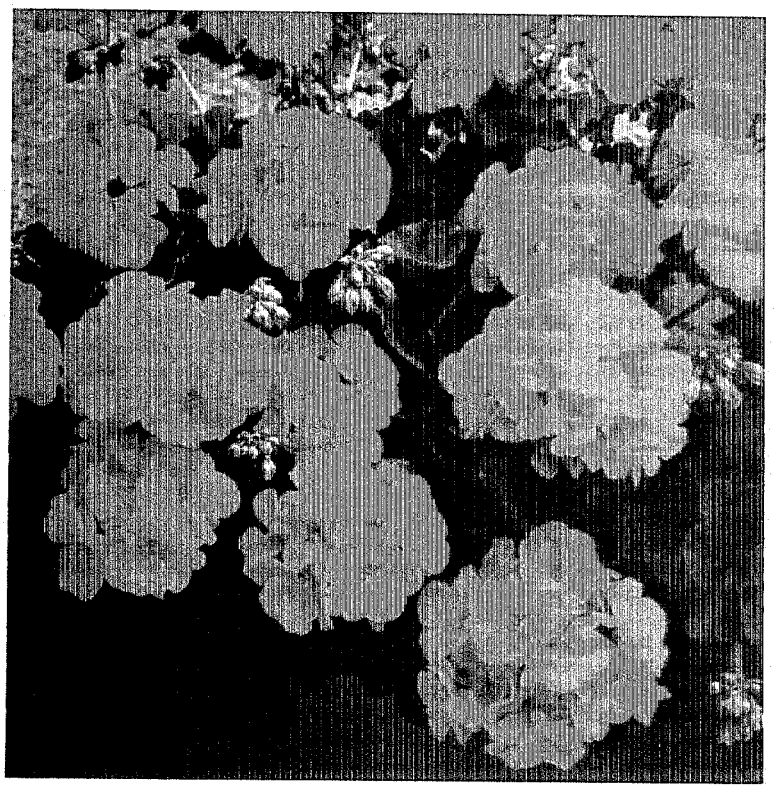
FIG. 2 illustrates the mature flower.

The following detailed descriptions set forth the distinctive characteristics of Americana Dark Red. The data which defines these characteristics were collected from asexual reproductions carried out by Goldsmith Seeds, Inc. in Gilroy, Calif. The plant history was taken on 11 week old plants, blossomed under natural light in a greenhouse and color readings were taken in the greenhouse (in Gilroy, Calif.) on Nov. 11, 1994 at 11:00 a.m. under ambient light. Color references are primarily to the RHS Colour Chart of The Royal Horticultural Society of London (RHS).

The Plant

Classification:

*Botanical.*—*Pelargonium hortorum* Bailey.

*Commercial.*—Zonal geranium.

Form:

Height: 11 to 13 cm, as a 4 inch pot plant, excluding blooms.

Strength: Early flowering with a basal branching tendency. Good shipping ability as rooted or unrooted cuttings.

Foliage: Abundant quantity.

*Leaves.*—Size: Diameter about 9 cm. Shape: Rounded cordate with occasional upfolding between veins. Margin: Irregularly crenate. Texture: Leathery and pubescent on both surface, especially along veins. Ribs and veins: Distinctly palmate, 3.5 to 4.5 cm long. Color: Upper side: Green. Under side: Lighter green color. Ribs and veins not prominently different from under surface. Petioles: About 7 to 7.5 cm in length.

The Bud

Size:

*Diameter.*—About 8 cm.

*Length.*—About 1.2 cm to 1.5 cm at time of bud opening.

Shape: Pointed ovoid.

Color: Petals when sepals first divide is 67A, RHS.

Sepals: 5 in number, flat behind petals. Pointed linear lanceolate, 146C RHS in an open flower.

The Flower

Blooming habit: Continuous throughout the year.

Size: Approximately 6 cm diameter, 1 cm deep, irregularly radially symmetrical.

Form: Cup-shaped when bloom first opens, later flattening to shallow cup shape with maturity.

Petals: 6 imbricate outer petals, 2.3–2.7 cm wide and approximately 2.8 cm long. Three to five inner smaller petaloids of varying shape. Both the outer petals and inner petaloids are dark red 45B RHS margin. Color changing little with age. Underside of petals lighter. Petals and petaloids soft and satiny.

Pedicel: Approximately 2.5–3.2 cm in length.

Persistence: Non-shattering flower.

Inflorescence

Type: An umbrel composed of approximately 22 flowers, erect or laterally ascending.

Peduncle: Green in color. Approximately 11.5 cm in length.

Reproductive Organs

Stamens:

*Anthers.*—5 normal and several malformed ones positioned below the mature stigma, dull red prior to anthesis.

*Filaments.*—White near base and mid-length, graduating to dull red near anther.

*Pollen.*—Orange in color.

Pistil:

*Number.*—1.

*Length.*—Approximately 8 mm.

*Stigma.*—5 linear lobes of near equal length, curling back toward ovary, purplish-red.

*Style.*—Length: About 4 mm. Color: Purplish red.

*Ovaries.*—At anthesis, densely pubescent with white hairs, oblong. Green drying to a light brown at maturity.

*Fruit.*—Partially fertile.

I claim:

1. A new and distinct cultivar of geranium substantially as herein shown and described, named Americana Dark Red, that is characterized by: green foliage with faint zonation, dark red color, and semi-double flowers on lare umbels, fast rooting and vigorous growth.

* * * * *